United States Patent [19]

Reeder et al.

[11] Patent Number: 5,312,589
[45] Date of Patent: May 17, 1994

[54] GAS TRANSFER APPARATUS

[75] Inventors: Gary D. Reeder, Morrison, Colo.; Thomas C. Robinson, Berkeley, Calif.; Thomas P. Sahines, Milpitas, Calif.; Robert K. Fernandez, Santa Clara, Calif.

[73] Assignee: Electromedics, Inc., Parker, Colo.

[21] Appl. No.: 19,400

[22] Filed: Mar. 4, 1993

[51] Int. Cl.$^5$ .............................................. A61M 1/14
[52] U.S. Cl. ................................ 422/45; 422/45; 422/48
[58] Field of Search ........................ 422/45, 46, 48, 47

[56] References Cited

U.S. PATENT DOCUMENTS

| | | | |
|---|---|---|---|
| 3,342,729 | 9/1967 | Strand | 422/48 |
| 3,794,468 | 2/1974 | Leonard | 422/48 |
| 3,998,593 | 12/1976 | Yoshida et al. | 422/46 |
| 4,111,659 | 9/1978 | Bowley | 422/48 |
| 4,231,878 | 11/1980 | Esmond | 210/321 |
| 4,256,692 | 3/1981 | Cover | 422/48 |
| 4,272,373 | 6/1981 | Stenberg et al. | 422/48 |
| 4,411,872 | 10/1983 | Bramson | 422/46 |
| 4,622,206 | 11/1986 | Torgeson | 422/48 |
| 4,722,829 | 2/1988 | Giter | 422/46 |
| 4,791,054 | 12/1988 | Hamada et al. | |
| 4,808,378 | 2/1989 | Nakanishi et al. | 422/48 |
| 4,906,581 | 3/1990 | Baker et al. | 436/147 |
| 4,940,617 | 7/1990 | Baurmeister | 428/363 |
| 4,975,247 | 12/1990 | Badolato et al. | 422/48 |
| 5,124,127 | 6/1992 | Jones et al. | 422/48 |
| 5,137,531 | 8/1992 | Lee et al. | 422/48 |
| 5,188,801 | 2/1993 | Fini | 422/48 |

FOREIGN PATENT DOCUMENTS

WO8900864  2/1989  PCT Int'l Appl.

Primary Examiner—James C. Housel
Assistant Examiner—Lien Tran
Attorney, Agent, or Firm—Gary M. Polumbus

[57] ABSTRACT

A gas transfer apparatus readily adapted for oxygenating blood includes a housing with a hollow internal chamber having a fiber mat consisting of two sets of intermingled hollow fibers with one set of fibers having micropores formed in the walls thereof and the other set having solid liquid impermeable walls. The housing for the apparatus is designed such that the blood being processed passes substantially uniformly across the entire cross section of the fiber mat whereby a treating gas such as oxygen being directed through the microporous fibers can be diffused into the oxygen deficient blood while excess $CO_2$ in the blood can cross diffuse into the interior of the fiber and be removed from the apparatus. Simultaneously with the cross diffusion of gas between the microporous fibers and the blood, a thermal conducting fluid such as water is passed through the solid walled fibers to maintain or regulate the temperature of the blood in the apparatus. The microporous and solid walled fibers may be woven in layers which are laminated to form a predetermined mat thickness separated by layers with only parallel fibers of a single set in each layer.

16 Claims, 4 Drawing Sheets

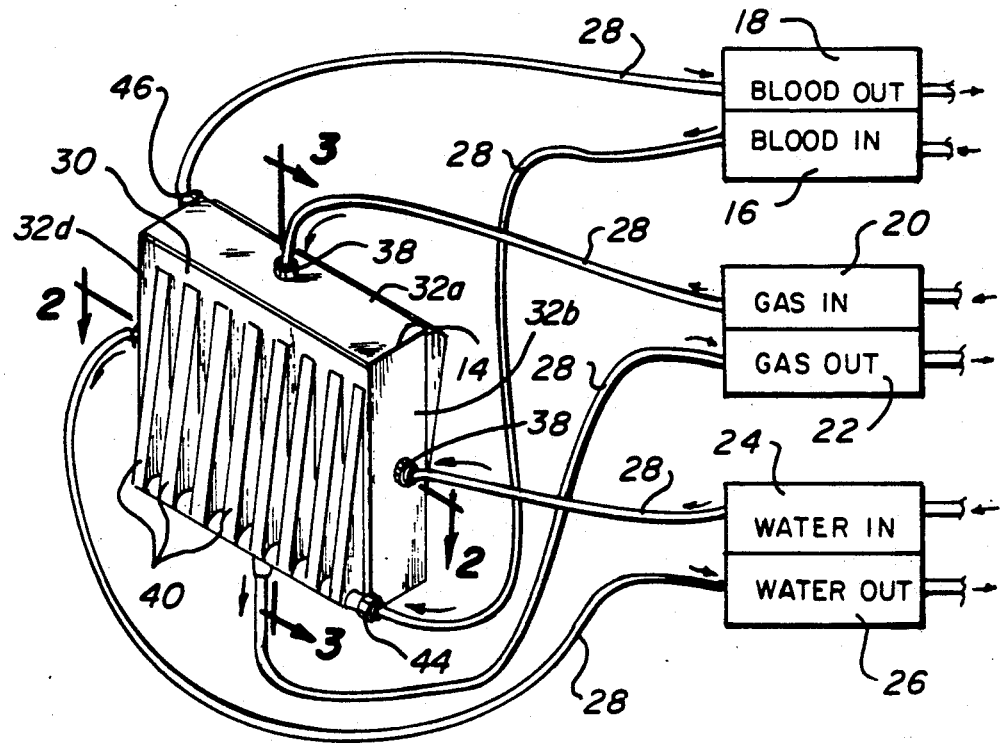
Fig_1
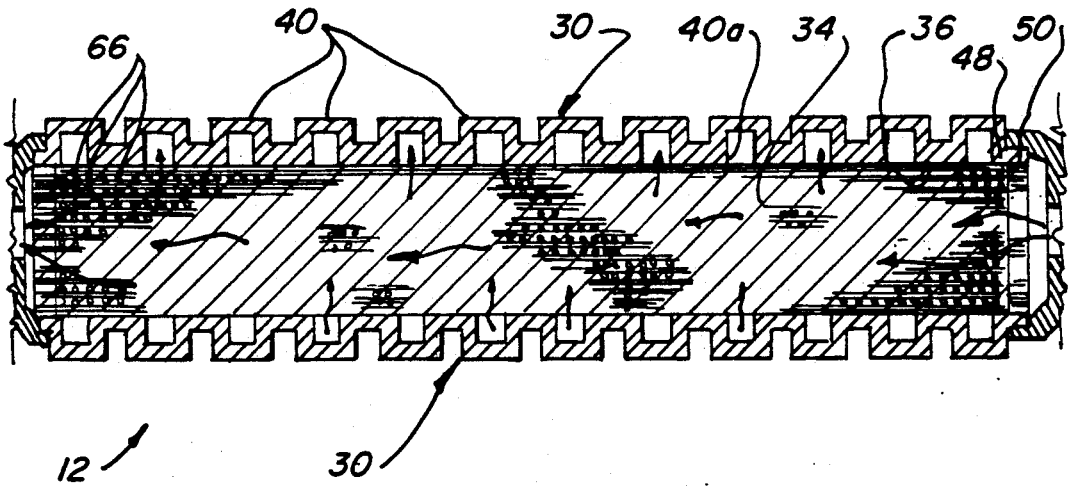
Fig_2

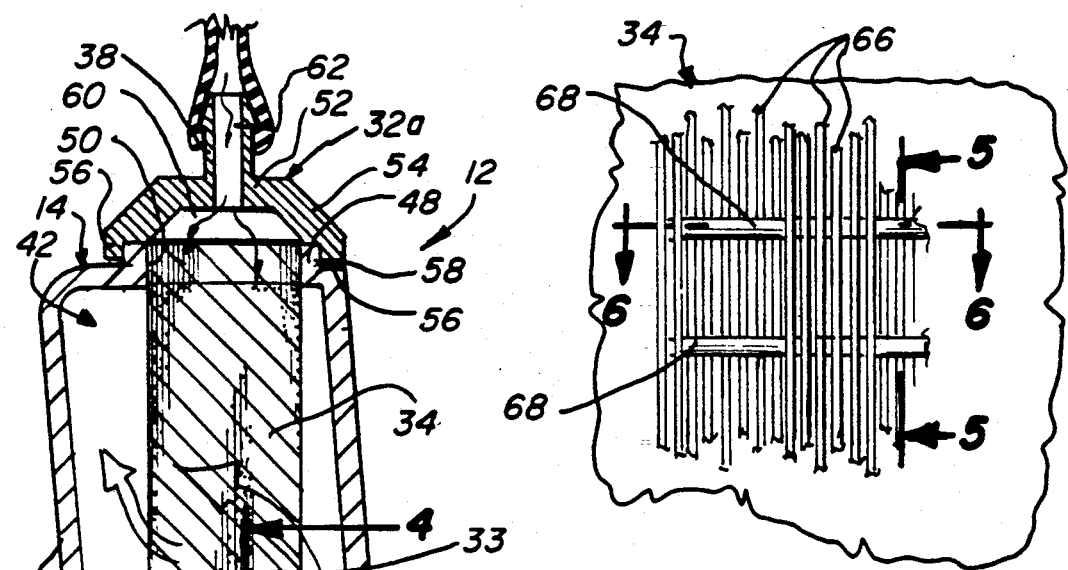
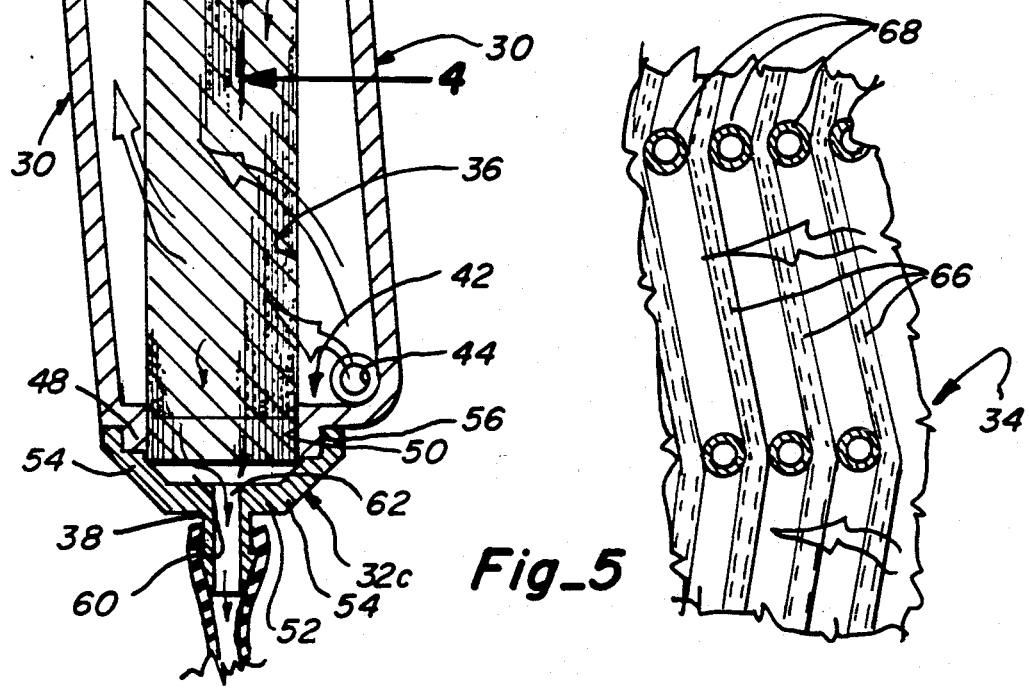
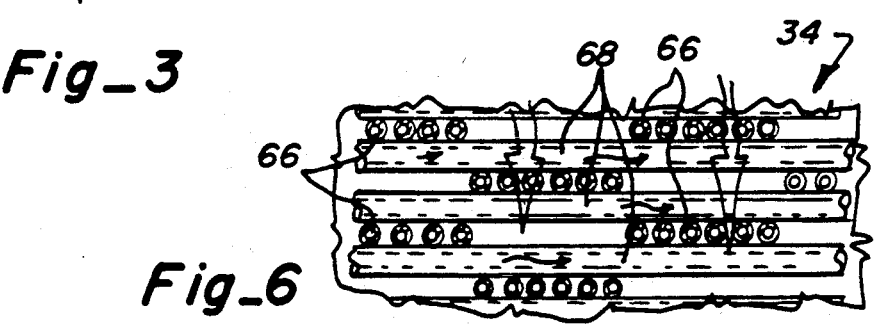

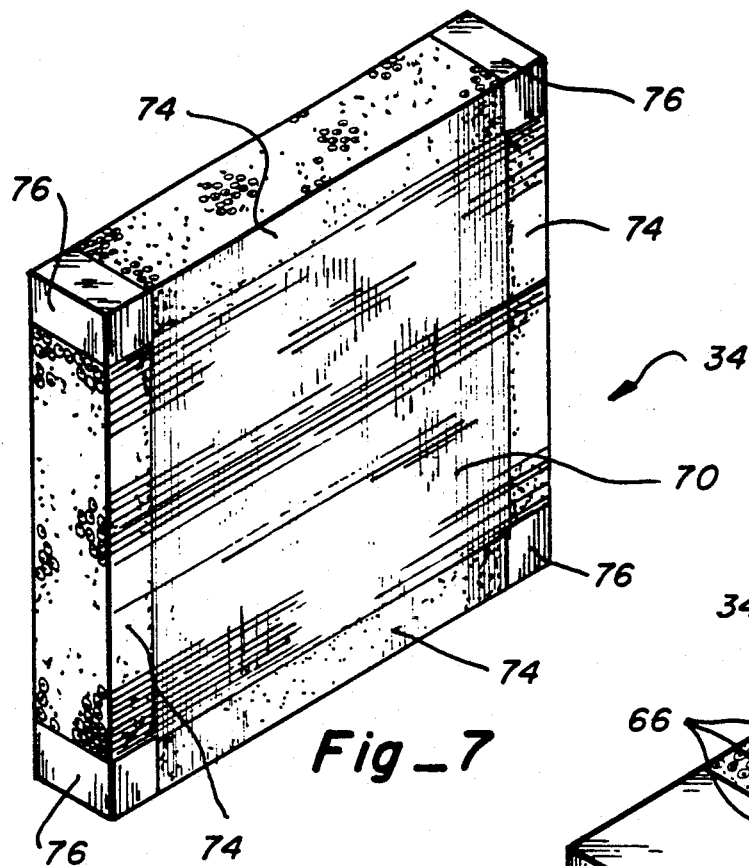
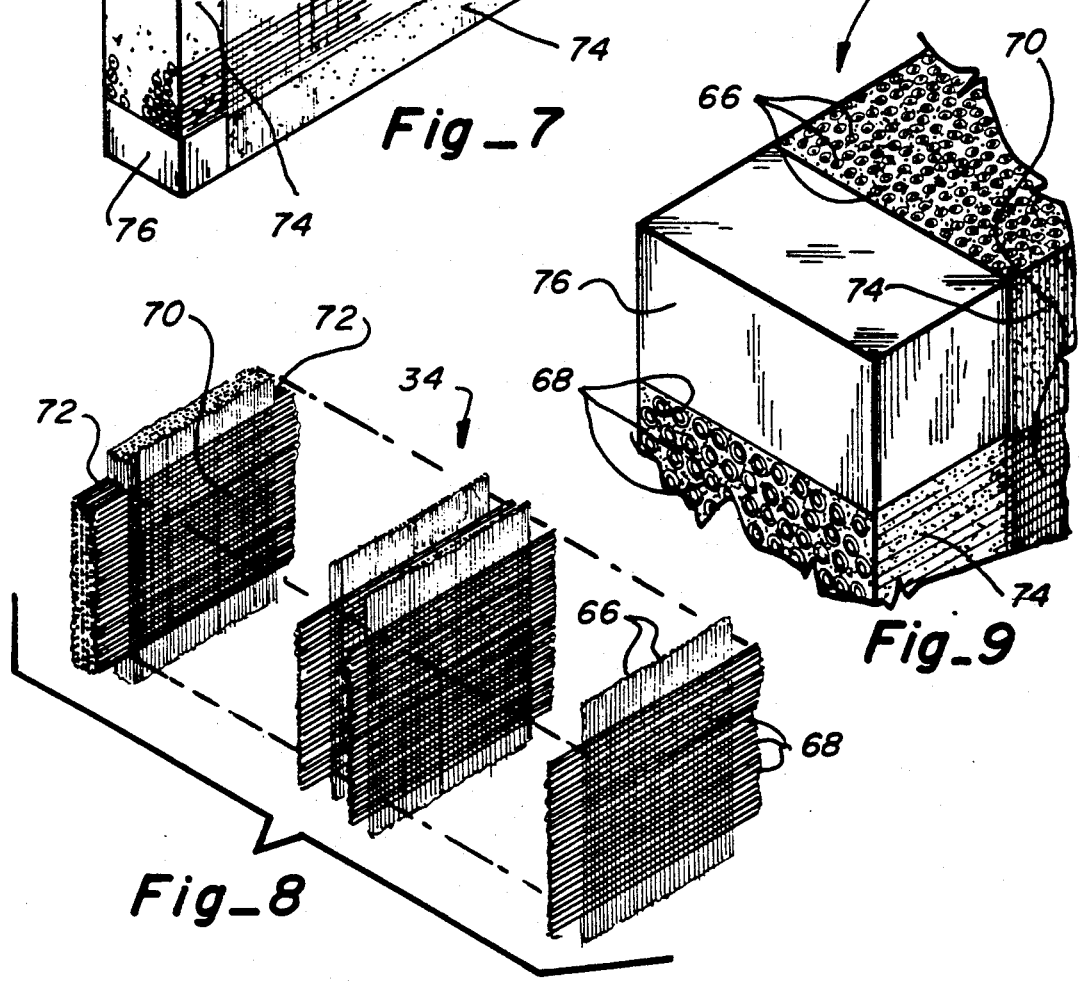

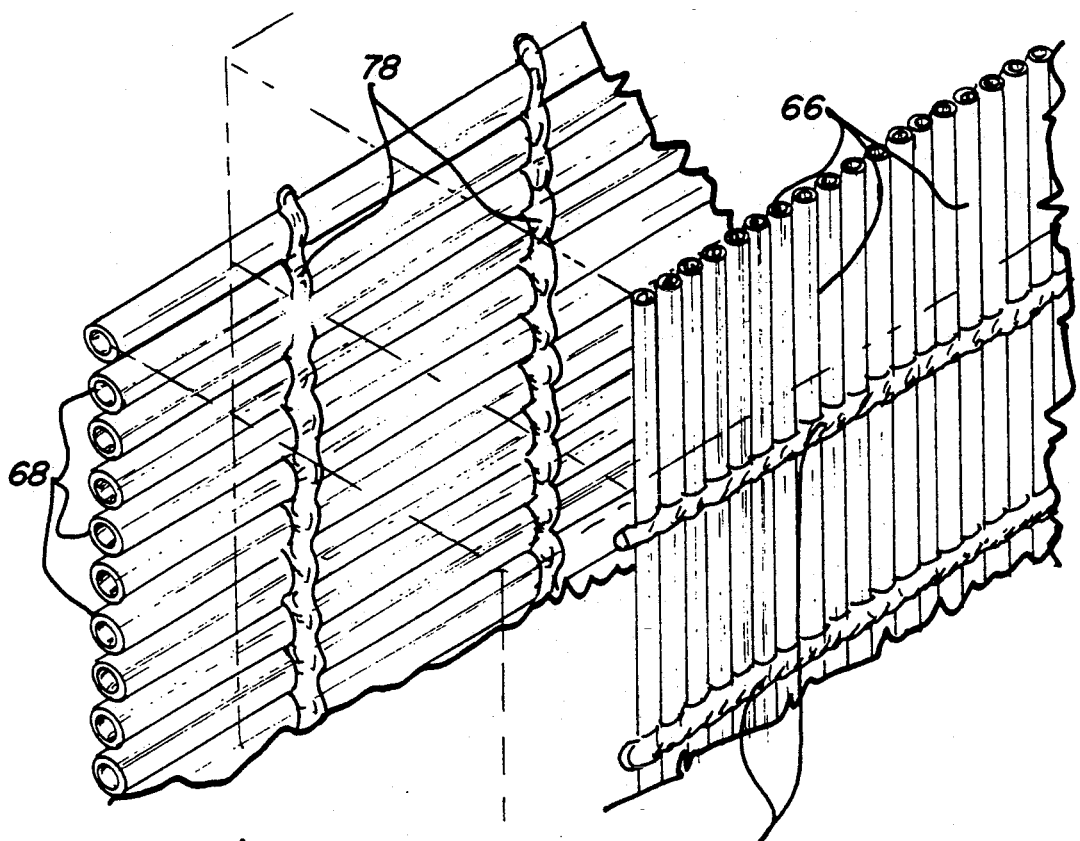
Fig_10
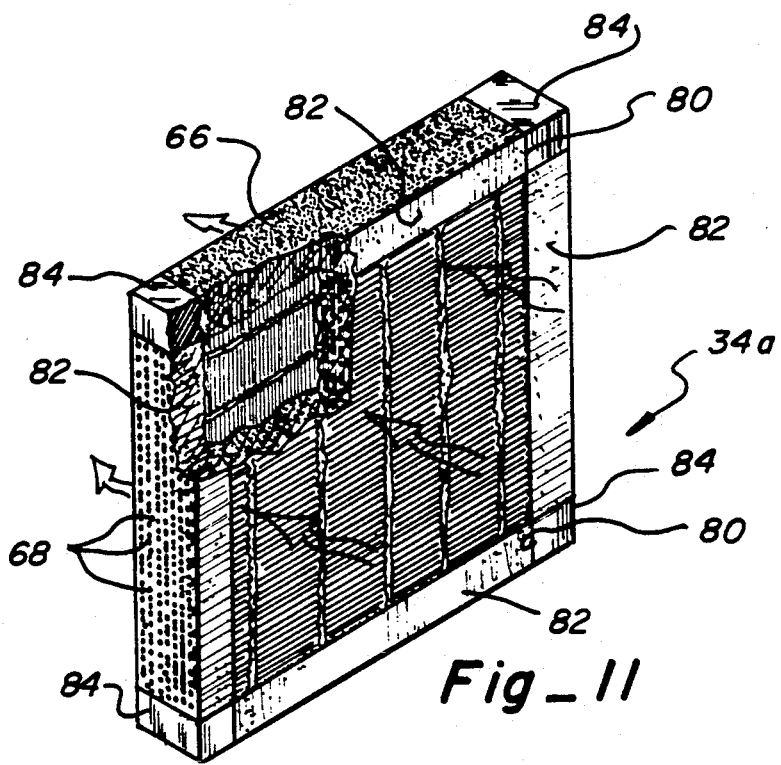
Fig_11

GAS TRANSFER APPARATUS

BACKGROUND OF THE INVENTION

1. Field of the Invention

The present invention relates generally to gas transfer systems and more specifically to an extracorporeal blood oxygenator utilizing microporous fibers.

2. Description of the Prior Art

In the late 1970s, technology was developed to allow the extrusion of very thin hollow tubes from polymeric materials. Additional benefits of this technology allowed for the creation of a multiplicity of micropores within the wall of such tubing. Such microporous hollow fibers (MHF) were soon readily adapted for use in extracorporeal blood oxygenators, serving as the membranous element separating blood from the gaseous phase, in order to minimize the blood trauma experienced when blood is directly mixed with gases.

Predating the development of MHF, blood oxygenators had been constructed so as to directly mix gaseous oxygen with the blood to achieve the necessary gas transfer. As previously stated, this resulted in significant blood trauma and necessitated the subsequent defoaming of the blood/gas mixture prior to return of the blood to the patient's arterial circulation. A significant incidence of patient pathology, such as gaseous embolization and silicone defoaming agent embolization to the brain and other major organs, when utilizing such bubble oxygenators led early investigators to develop a potentially safer device called a membrane oxygenator.

Early membrane oxygenator designs utilized flat sheets of membranous material (usually thin silicone rubber sheets) to separate the alternating blood and gas channels of the device. The membrane material was arranged in either a flat stack, referred to as a flat plate oxygenator or as a continuous coil around a central core, referred to as a spiral coil oxygenator. Blood was allowed to flow within the channel between two opposing membrane layers, while gaseous oxygen flowed within the adjacent channels on the other side of the membrane sheets. The necessary transfer of oxygen molecules into the blood and the simultaneous removal of carbon dioxide molecules from the blood was by passive diffusion and was limited by the chemical solubility of the gases in the membrane material. While many of these early devices were functional, and were utilized clinically, they were relatively inefficient gas transfer devices requiring large membrane surface areas to provide adequate gas exchange. An additional problem with the earlier designs was the necessary compression and/or membrane tension required to keep the membranes from bulging apart during active blood flow. Such bulging resulted in undesirably thick blood film thickness within the device and caused further deterioration of gas transfer efficiency and increased fluid priming volume requirements.

With the development of microporous polymeric materials, a hybrid design was possible combining the gas transfer efficiency benefits of a direct blood gas interface (as in the bubble oxygenator) with the reduced blood trauma benefits of a membrane device. The molecules of gas transiting between phases within the device no longer had to physically dissolve within the membrane material in order to pass between channels, as gas molecules could directly pass through the fluid/gas film interface created within the micropores of the membrane. Passage of gross gaseous emboli into the blood channels was prevented, due to the high surface tension of the plasma fluid film at the surface of the microscopic pores of the membrane material. Early use of microporous polymeric sheets in flat plate designs encountered the same problems of control of blood film thickness as previously mentioned. The emergence of MHF, however, allowed more consistent control of this previously difficult variable in membrane oxygenator design, by providing a fixed dimension lumen within the fiber for the passage of blood while simultaneously bathing the exterior of the MHF with oxygen gas. Such early MHF membrane oxygenators utilized a linear bundle of fibers, the ends of which were first sealed within a block of polymeric material followed by the reopening of each end of the fiber lumens by cleanly slicing off the distal edge of the cured resin blocks. In this manner, direct communication of the gas and blood passages was prevented at the terminal ends of the fiber bundle.

The early luminal blood flow MHF membrane oxygenators, generally referred to as "internal flow configuration oxygenators," were eventually supplanted by development of "external flow configuration oxygenators" in which the blood flow passed over the external surface of the MHF while gaseous oxygen was allowed to flow within the internal lumen of the MHF. Such a design change evolved due to the high fluid pressures which occurred as a result of passing relatively viscous fluid through extremely narrow fiber lumens within the "internal flow configuration oxygenators". Initial "external flow configuration oxygenator" designs utilized the same linear fiber bundle, requiring various techniques of fiber bundle compression to maintain the smallest blood film possible around each fiber. Subsequently it was found that by controlled tension spiral winding of the MHF around a central core, a tubular core of MHF could be created which more closely controlled the blood film thickness, or boundary layer. Controlling the boundary layer in this manner allowed the adult membrane oxygenator total fiber surface area to be reduced from approximately 4.5 square meters to 2.0 square meters due to boundary improvement in gas exchange efficiency. The spiral wound membrane oxygenator is currently the most popular design, due to its efficiency, in spite of significant manufacturing difficulties with the uniform creation of the spiral wound fiber cores.

Recently, other methods for control of boundary layer and external flow configuration MHF membrane oxygenators have appeared in the market place. One such method is the bundling of MHF fibers into "fiber ribbons" by tightly wrapping a small fiber bundle with a retaining thread. These bundles are then placed within a channel in a metallic coil, which serves both as a blood flow channel and a thermal exchange surface.

A second functional feature required for the successful use of a membrane oxygenator in cardiopulmonary support of the cardiac surgical patient is that of heat exchange. Provision for adequate thermal exchange within the cardiopulmonary bypass circuit must be made in order to maintain and/or alter the patient's body temperature during the surgical procedure. This is most commonly achieved by utilizing a blood oxygenator which has an integral heat exchanger as part of its design, although this function may also be accomplished by inclusion of a separate heat exchanger somewhere within the extracorporeal circuit. With early bubble oxygenators, the integral heat exchangers were placed on the outflow, or arterial, side of the oxygenator such that heat exchange occurred after the gas exchange process had been completed. It was found, however, that when warming the blood in such configurations micro bubbles of gas could be detected, due to the decreased solubility of gases in a fluid as temperature of the solution is increased. Accordingly, subsequent designs provided for heat exchanger placement on the inlet, or venous, side of the oxygenator.

It is of interest to note that all currently utilized oxygenators have either venous or arterial side heat exchangers, with the exception of the aforedescribed device utilizing "fiber ribbons" in a metallic coil. The metallic blood channels, within which the fiber ribbons are placed, serve as a thermal exchange surface, as the undersurface of the metallic coil is fitted with water conduits. By passing thermally conditioned water through these conduits, the metallic coil can be either heated or cooled, to achieve blood heat exchange within the same channels utilized for gas exchange.

It is important in any blood oxygenator that it provide an efficient system for transferring gas to and from the circulating blood. It is also of critical importance that the device be capable of cooling the blood being recirculated into the patient's vascular system so that the patient's body temperature can be cooled to produce a physiologically protective hypothermic state. It is conversely important that the device be capable of warming the blood so that near the end of a surgical procedure, the device can warm the recirculating blood that is returning to the patient to a normothermic state.

Another important feature of a membrane oxygenator is that it has a minimal fluid priming volume. The cardiopulmonary bypass circuit is normally composed of numerous components, with the oxygenator and other components interconnected by significant lengths of sterile tubing. Additional lengths of tubing are connected to the patient's vascular system and are utilized to direct the patient's venous blood into the extracorporeal circuit, and to return the arterialized blood to the patient's arterial circulation. This circuit must be completely filled with an appropriate physiologic fluid, prior to connection into the patient's vascular system to prevent catastrophic embolization of gas into the circulatory system of the patient. Obviously, the larger the total fluid volume of the bypass circuit, the greater the hemodilutional effect on the patient. As one progressively dilutes the patient's blood, a critical point will be reached at which the patient's blood will not be able to transport sufficient oxygen to support tissue requirements without excessive blood flow rates. Such extreme hemodilution will then require transfusion of homologous blood into the circuit to increase the blood's oxygen-carrying capacity. Consequently, the optimal design of an oxygenator would be to minimize the fluid priming volume required for safe operation.

Still another important feature of a blood oxygenator is that it exert minimal trauma on the blood. Blood trauma can occur in many different ways with the most significant cause being that of excessive sheer forces acting upon the blood elements flowing through the device. In the optimal design for a membrane oxygenator, one must balance the need for an extremely thin boundary layer of blood next to the membrane (to maximize gas transfer) with the need to keep blood velocity minimized (to reduce sheer force induced blood trauma).

Obviously, in light of the fact that blood oxygenators are used in critical surgery such as cardiopulmonary bypass, it is extremely important that the device perform predictably and reliably. It is also important due to the increasing costs of medical care that the cost of manufacturing be minimal.

Several patents have been issued for devices developed to address individually or in combination some of the issues raised hereinabove. By way of example, U.S. Pat. No. 4,791,054 to Hamada, et al., U.S. Pat. No. 4,111,659 issued to Bowley, U.S. Pat. No. 3,998,593 issued to Yoshida, et al. and U.S. Pat. No. 5,137,531 issued to Lee, et al. all concern oxygenator type devices wherein the oxygenator has separate and distinct chambers for oxygenation and temperature control.

U.S. Pat. No. 3,342,729 issued to Strand discloses a permeability separatory cell that utilizes a mesh membrane of fibers having cation exchange properties running in one direction and fibers having anion exchange properties in a perpendicular direction. U.S. Pat. No. 3,794,468 issued to Leonard discloses a mass transfer device having a wound tubular diffusion membrane. U.S. Pat. No. 4,722,829 issued to Giter is another illustration of a blood oxygenator wherein tubes through which treating gas flows include spherical lobes which are interengaged to define small passages through which the blood moves. Finally, U.S. Pat. No. 4,940,617 issued to Baurmeister discloses a multilayered hollow fiber wound body wherein the fibers are wound either in helices or spirals.

It is to address the issues identified above and to resolve the issues in a more satisfactory manner than the existing prior art that the present invention has been developed.

SUMMARY OF THE INVENTION

The present invention relates to a gas transfer apparatus which functions effectively as a blood oxygenator and that finds primary use in an extracorporeal oxygenating system. For purposes of the present disclosure, the apparatus will be described in connection with its use as a blood oxygenator.

The apparatus includes a housing with an internal blood processing chamber in which is disposed a mat consisting of two sets of intermingled fluid conducting fibers. The fibers of one set have micropores formed in the walls thereof to permit cross-diffusion of gases while the fibers of the other set have solid liquid impermeable walls. Manifolds are provided at opposite ends of each set of fibers and inlet and outlet means are provided in the housing to conduct the blood that is being treated through the housing across the mat of fibers. The microporous set of fibers is adapted to transmit a gas treating fluid while the solid walled set of fibers is adapted to conduct a thermal conducting fluid. The manifolds associated with each set of fibers have connectors to permit the ingress and egress of fluids to the fibers associated therewith.

With the apparatus of the present invention, the blood is admitted to one side of the housing and removed from the opposite side of the housing after it has passed through the mat of fibers. The set of fibers having micropores in the walls thereof can be used to transmit oxygen so that cross diffusion of gases through the walls of the fibers is permitted. The oxygen in the fibers diffuses into the oxygen deficient blood passing through the internal chamber while excess $CO_2$ in the blood cross-diffuses into the fibers. The solid walled fibers are used to transmit a thermal conducting fluid such as water so that the temperature of the blood is regulated and/or maintained simultaneously with the cross diffusion of gas.

In one embodiment of the invention, the sets of fibers are woven in separate layers which can be superimposed on top of each other forming a mat of such woven fibers. The thickness of the mat is selected depending upon the required surface area of the fibers desired for a predetermined flow rate of blood through the apparatus.

In another embodiment, the microporous fibers are secured together in separate layers with the microporous fibers in each layer extending in parallel relation. Spaced transverse beads of adhesive are extended across the fibers of each layer to bond the fibers together in a predetermined side-by-side relationship. The liquid impermeable fibers are similarly bonded together in separate layers so that layers of microporous fibers and liquid impermeable fibers can be stacked in a mat of a predetermined thickness depending upon the required surface area of the fibers desired for a predetermined flow rate of blood through the apparatus.

Other aspects, features and details of the present invention can be more completely understood by reference to the following detailed description of a preferred embodiment, taken in conjunction with the drawings, and from the appended claims.

BRIEF DESCRIPTION OF THE DRAWINGS

FIG. 1 is a diagrammatic isometric view of the apparatus of the present invention connected to supplies of treating and thermal conducting fluids as well as blood.

FIG. 2 is an enlarged horizontal section taken along line 2—2 of FIG. 1.

FIG. 3 is an enlarged vertical section taken along line 3—3 of FIG. 1.

FIG. 4 is an enlarged fragmentary section taken along line 4—4 of FIG. 3.

FIG. 5 is an enlarged fragmentary section taken along line 5—5 of FIG. 4.

FIG. 6 is an enlarged fragmentary section taken along line 6—6 of FIG. 4.

FIG. 7 is an isometric view of a mat consisting of multiple layers of woven fibers.

FIG. 8 is an exploded isometric view of a plurality of layers of woven fibers.

FIG. 9 is a fragmentary isometric view of one corner of the fiber mat illustrated in FIG. 7 showing the exposed open ends of fibers of each set and a spacer block in the corner of the mat fiber assembly.

FIG. 10 is a fragmentary exploded isometric view of a second embodiment of a mat for use in the apparatus of the present invention.

FIG. 11 is an assembled isometric view of the mat of FIG. 10.

DESCRIPTION OF THE PREFERRED EMBODIMENTS

For purposes of illustration, the gas transfer apparatus of the present invention will be described in connection with one of its known uses and specifically in connection with the oxygenation of blood. The apparatus will therefore be conveniently referred to as a blood oxygenator 12.

With reference to FIG. 1, the blood oxygenator 12 can be seen to include a housing 14 having a plurality of external connectors so that the housing can transmit therethrough a fluid to be treated (blood), a treating fluid (oxygen), and a thermal transfer fluid (water). Since systems for transmitting the aforedescribed fluids to and from the apparatus could take many different forms, they have merely been illustrated diagrammatically as blood inlet system 16, blood outlet system 18, gas inlet system 20, gas outlet system 22, water inlet system 24 and water outlet system 26. Each of the aforedescribed inlet or outlet systems are associated with a flexible conduit 28 that is operatively interconnected with the apparatus in a manner to be described more fully hereafter and includes either a pressure or vacuum pump which has not been shown. A pressure pump could be used to force the associated fluid through the apparatus under positive pressure, or a vacuum pump could be used to draw the fluid through the apparatus under a negative pressure.

As is probably best illustrated in FIGS. 1 and 3, the housing 14 includes a pair of identical opposed face plates 30 which are interconnected along their peripheries and retained in inverted spaced relationship by four manifold members 32a, 32b, 32c and 32d which in combination define a peripheral frame. The manifolds retain the face plates 30 in a predetermined spacing adapted to accommodate a fiber mat 34 which bridges the entire cross section of the face plates. The mat is disposed in an internal chamber 36 defined by the housing 14 such that the flow of blood through the housing must pass through the mat.

The mat 34 which will be described in more detail later, consists of two sets of hollow fibers which are disposed in substantially mutually perpendicular relationship to each other. The fibers of one set have micropores formed in a wall thereof and are adapted to transmit the oxygen treating gas while the fibers of the other set have solid liquid impermeable walls and are adapted to transmit the thermal conducting water. The opposite ends of the fibers of each set are open and are in communication with one of the four manifolds 32a–32d. The manifolds themselves are separated hermetically as will be more fully explained later.

The manifolds 32a–32d are each provided with a connector 38 establishing communication between the interior of the manifold and the environment surrounding the housing 14 so that the treating Oxygen gas can be transferred from one manifold 32a to an opposite manifold 32c through the microporous fibers while the thermal conducting water can be passed from a mutually perpendicular manifold 32b to its opposing manifold 32d through the solid walled fibers. In this manner, the blood that is treated in the apparatus simultaneously takes on oxygen and relinquishes carbon dioxide in a known manner while being thermally treated to either raise, lower or maintain its temperature.

With reference to FIGS. 1-3, the opposing face plates 30 can be seen to be of quadrangular configuration each having a plurality of vertically extending hollow parallel ribs 40 of triangular, longitudinal cross section which define elongated channels 40a of u-shaped transverse cross section (FIGS. 1-3). It will be apparent from the description that follows that the ribs 40 do not have to extend vertically but as illustrated in FIG. 1 and for purposes of the present description, the ribs are oriented vertically. Due to the triangular longitudinal configuration of the ribs, they define in aggregate a header region 42 along one edge of the associated face plate and diminish in depth as they extend toward the opposite edge of the face plate. In the arrangement illustrated, the header region 42 of one face plate is disposed along one edge of the apparatus while the header region on the opposite face plate is disposed along the opposite edge of the apparatus due to the inverted relationship of the face plates.

The face plate 30 on one side of the apparatus has an inlet port/connector 44 formed in an outermost triangular rib 40 with the inlet port/connector communicating directly with the header region 42 of the face plate. The inlet port/connector 44 has a frustoconical head suitable for hermetic connection to a flexible hose or conduit 25 so that the flexible hose connected to the blood inlet system 16 can be releasably affixed thereto. The opposite face plate includes an outlet port/connector 46 formed in an outermost triangular rib 40 along the opposite edge of the apparatus with the outlet port/connector 46 being in direct communication with the header region 42 of the associated face plate. The outlet port/connector 46 has a frustoconical head suitable for releasable hermetic connection to the flexible hose 28 associated with the blood outlet system 18. It can therefore be appreciated that blood is permitted to enter the apparatus 12 through the inlet port/connector and pass through the apparatus for removal through the outlet port/connector which is at an opposite corner of the apparatus and on the opposite side of the apparatus from the mat 34 of hollow fibers.

As best seen in FIG. 3, each face plate has an outwardly directed ridge 48 formed along its periphery to facilitate attachment of the face plate to the four manifolds 32a–32d. The ridge 48 defines an inwardly directed face 50 adapted to abut with the hollow fiber mat 34 in a manner to be described in more detail hereafter.

The face plates as well as the manifolds can be made of any suitable material such as an inert plastic, stainless steel or other such material which does not react with the blood, treating gases or thermal conducting water.

The four manifolds 32a–32d are of identical construction and in transverse cross section are of generally hollow trapezoidal configuration (FIG. 3). Each manifold includes an outer plate portion 52 and obliquely directed side walls 54 diverging from opposite side edges of the outer plate portion 52. The distal edges of the side walls have ribs 56 which project in a direction perpendicularly to the outer plate portion 52 and are adapted to laterally engage outwardly directed faces 58 of the peripheral ridges of the face plates. The junctures of the ribs 56 on the manifolds and the ridge 48 on the face plates are hermetically sealed, as by sonic welding, thereby fully integrating the housing 44 for the apparatus 12 and defining the sealed internal chamber 36. As will be appreciated by reference to FIGS. 2 and 3, each manifold defines a hollow space 60 in communication with one side edge of the hollow fiber mat 34 for a purpose that will become more clear hereafter.

Each manifold 32a–32d has a port 62 formed therein and associated with a connector 38 with a frustoconical head so that flexible tubing 28 associated with the treating gas or the thermal conducting water can be hermetically connected thereto. Each connector 38 is hollow so that fluids can be passed therethrough to the hollow space 60 within the associated manifold.

The hollow fiber mat 34 is probably best illustrated in FIGS. 5–9 to include layers of woven fibers. The layers are placeable in face-to-face relationship when assembling the mat. The fibers 66 in one set, as illustrated in FIGS. 3 and 7 through 9, extend vertically while the fibers 68 in a second set horizontally. The fibers 66 of the one set have micropores formed in the walls thereof to permit the cross diffusion of gases between the blood and the hollow interior of the fibers and the fibers 68 of the second set have solid liquid impermeable walls to confine and transmit the thermal conducting water. The fibers can be woven in any desired pattern with one microporous fiber 66 per one solid walled fiber 68 or in various ratios of such fibers. In other words, if it be determined that control of the temperature of the blood can be accomplished with one-fourth the number of solid walled fibers as are required for the desired cross diffusion of gases, there might be four microporous fibers woven per solid walled fiber. In FIGS. 4 through 6, the ratio is six microporous fibers 66 to one solid walled fiber 68 for illustration purposes only.

A number of layers of woven hollow fibers are assembled in face-to-face relationship dependent upon the surface area of the fibers desired for a given flow rate of blood through the apparatus. The rate of cross diffusion of gas per given volume of exposed blood is known for certain microporous fiber constructions and accordingly, depending upon the flow rate of the blood through the apparatus, the number of microporous fibers are known and thus the number of fiber layers can be determined.

As can be readily appreciated by reference to FIG. 8, the layers of woven fibers 66 and 68 are formed so that the fibers of each set extend a predetermined distance beyond a center woven section 70 of the layer. Thus when the layers are assembled in face-to-face relationship, it can be seen that the layers define a generally four sided planar figure having substantially square shaped notches 72 formed in each corner thereof.

The ends of the fibers of both sets are potted in a resinous potting compound 74 such as polyurethane, readily known and available in the art, which functions to integrate and bond the layers of the woven fibers along the four edges thereof. In a known manner, the potting compound is sliced so as to remove terminal ends of the fibers leaving each fiber open at its opposite ends. After the layers have been potted together and the potting sliced to expose open ends of the fibers, the notches 72 in the four corners of the composite mat are filled with corner or spacer blocks 76 of inert material such as polyurethane or stainless steel with the corner blocks having a quadrangular cross section. Once the corner blocks have been positioned and secured in the notches in any suitable manner, it can be seen in FIG. 7 that the mat of hollow fibers is a planar four sided structure that has been presized to fit within the housing 14 and particularly so that the outer edges of the fiber mat engage the inwardly directed faces 50 of the ridge 48 on the face plates. The inwardly directed faces of the ridges are secured to the outer peripheral edge of the fiber mat 34 in any suitable manner to establish an hermetic seal. In actual assembly of the apparatus, the face plates 30 are secured to the fiber mat 34 before the manifolds 32a–32d are secured to the peripheral edge of the face plates in the manner previously described.

An alternative embodiment of the fiber mat is illustrated in FIG. 10 and referred to as a parallel fiber mat 34a. In this embodiment, each layer of the mat is comprised of fibers 66 or 68 of one distinct set with the fibers laid in parallel relationship and bonded transversely at spaced intervals by beads of adhesive 78. The side-by-side relationship of the fibers of a single set in each layer is predetermined for specific uses but by way of illustration, the microporous fibers 66 of the first set might be positioned in contiguous or slightly spaced parallel relationship while the solid walled fibers 68 of the second set might be positioned in a spaced parallel relationship wherein there is a greater space between adjacent fibers. Each layer of distinct fibers can then be stacked until a desired thickness or predetermined surface area of fibers has been established. While the microporous fibers 66 in different layers would be assembled to extend in the same direction and the solid walled fibers 68 of other layers in a substantially perpendicular direction, it would not necessarily be required that layers of the first and second sets of fibers alternate. In other words, there may be two layers of microporous fibers 66 for every one layer of solid walled fibers 68 depending upon the relative surface areas of the fibers of each set desired for a particular application.

Each layer of fibers is preferably formed in a rectangular configuration so that the length of a layer, which extends in the same direction as the fibers, is greater than its width. Thus when the layers are stacked in face-to-face relationship, a generally four sided mat is defined with notches 80 in each corner. The ends of the fibers are potted in a suitable potting compound 82 to integrate the layers into the unified mat 34a and the potting is subsequently sliced to expose open ends of the fibers. Corner blocks 84 are bonded or otherwise secured in the notches 80 in each corner of the mat to establish a four sided mat which is easily integrated into the housing 14 in a manner identical to that described previously in connection with the first embodiment of the mat.

While the fibers used in the mat are readily available and well known in the art, by way of example, the microporous fibers 66 might be of the type manufactured by Mitsubishi Rayon Co., Ltd. of Tokyo, Japan and sold under identification No. EHF 180M-1. For illustration purposes, microporous fibers having the following dimensions have been found suitable: inner diameter of 180 microns, outer diameter of 282 microns and a wall thickness of 49.5 microns. The solid walled fibers 68 are also available from the same source and are sold under identification No. HFE 430-4. The dimensions of solid walled hollow fibers found to be suitable are: inner diameter of 429 microns, outer diameter of 577 microns and a wall thickness of 73.5 microns.

Also in one preferred embodiment, when the fibers are woven to form the mat, 36 layers defining a thickness of 1.62 inches and providing an effective microporous fiber surface area of 2.45 square meters and a solid walled fiber surface area of 0.84 square meters provided adequate cross diffusion of gas to oxygenate the blood of an adult while giving some flexibility to the ability to regulate the temperature of the blood within acceptable ranges. The fibers were all nine inches long with the woven area being six inches square.

In the parallel fiber mat, one embodiment which has worked effectively included 60 layers of microporous fibers with an effective surface area of 2.51 square meters and 29 layers of solid walled fibers with an effective surface area of 1.32 square meters. The thickness of the mat was 1.33 inches. The fibers were all nine inches long and each layer was six inches wide so that the area of overlap of microporous fiber layers and solid walled fiber layers was six inches square.

In operation, the inlet and outlet ports 44 and 46, respectively, of each face plate 30 are connected to the flexible hoses 28 associated with the blood inlet system 16 and the blood outlet system 18 respectively which include pressure or vacuum pump means for moving the blood through the apparatus. It will be appreciated that since each face plate has a relatively large header region 42, the blood which is introduced to the internal chamber 36 of the apparatus in the header region will readily spread or flow across the apparatus before proceeding upwardly along each triangular rib 40 for dispersal across the entire cross section of the face plate and consequently the fiber mat 34 or 34a. The blood of course migrates across the fiber mat due to the pressure differential created by the blood inlet/outlet systems and once it has transversed the entire fiber mat, it is collected on the opposite side and removed from the apparatus through the outlet port 46 in the opposing face plate.

Simultaneously with the blood moving through the apparatus from one face plate to the other and across the fiber mat, oxygen gas is introduced to the manifold 32a associated with the inlet end of the microporous fibers 66 at the top of the apparatus 12 as shown in FIG. 1 and allowed to pass through the fibers in a vertically downward direction. As the oxygen gas passes through the fibers 66, a cross diffusion of gas occurs between the interior of the microporous fibers and the blood which is circulating around the exterior surfaces thereof. The principle of cross diffusion is well known in the art with the oxygen passing outwardly through the micropores and being absorbed by the oxygen deficient blood while excess $CO_2$ in the blood passes inwardly through the micropores to the hollow interior of the microporous fibers and is removed through the flexible hose 28 associated with the gas outlet manifold 32c at the bottom of the apparatus.

Also simultaneously, the thermal conducting water is introduced to the water inlet manifold 32b on the right side of the apparatus as viewed in FIG. 1 and allowed to pass horizontally through the hollow solid walled fibers 60 for removal from the apparatus on the left side through the outlet water manifold 32d and the flexible hose 28 associated therewith. As mentioned previously, the thermal conducting water can affect the temperature of the blood by raising the temperature, lowering the temperature or maintaining a temperature dependent upon the temperature of the water as it enters the apparatus. The hollow space 60 within each manifold allows the treating gas or thermal conducting water to enter substantially uniformly the open ends of the associated fibers so that the treating gas and thermal conducting water is uniformly distributed across the entire cross section of the fiber mat.

The gas transfer apparatus 12 of the present invention has been found to desirably oxygenate blood while simultaneously regulating the temperature of the blood in a manner that overcomes many of the shortcomings of prior art systems which have been devised for oxygenating blood. The simultaneous oxygenation and temperature regulation overcomes the shortcomings in numerous prior art systems which inherently must heat the oxygenated blood before or after the oxygenation takes place.

Although the present invention has been described with a certain degree of particularity, it is understood that the present disclosure has been made by way of example, and changes in detail or structure may be made without departing from the spirit of the invention, as defined in the appended claims.

We claim:

1. A gas transfer apparatus comprising in combination,
   a housing having an interior fluid processing chamber, at least one pair of manifolds with each manifold having a connector establishing communication between the manifold and the environment surrounding the housing, and an inlet and an outlet port means establishing communication between said interior chamber and the environment surrounding the housing to permit a fluid being processed to pass through said interior chamber,
   two distinct sets of intermingled elongated hollow fibers, the fibers of each set having two ends one set of fibers having outer walls with micropores formed therein to allow a gas to diffuse through the micropores into said fluid being processed and the second set having solid liquid and gas impermeable walls to selectively allow for the passage of a thermal transfer fluid, each end of said fibers in said one set being in fluid communication with one of said manifolds, said fibers being disposed in said interior chamber such that said fluid can be passed through said interior chamber via said inlet and outlet port means and said gas can be passed from one manifold to the other manifold through said one set of fibers.

2. The gas transfer apparatus of claim 1 wherein there are two pair of manifolds and wherein the second set of fibers are hollow and wherein each end of the fibers of the second set is in fluid communication with one of said manifolds of a second pair of manifolds, such that said thermal transfer fluid can be passed through said second set of fibers to regulate the temperature of the fluid passing through said interior chamber.

3. The gas transfer apparatus of claim 2 wherein there are unequal numbers of fibers in the two sets.

4. The gas transfer apparatus of claim 1 wherein the fibers of one set are woven with the fibers of the other set into a mat.

5. The gas transfer apparatus of claim 4 wherein there are unequal numbers of fibers in the two sets.

6. The gas transfer apparatus of claim 1 wherein the interior chamber is partially defined by a pair of opposed face plates.

7. The gas transfer apparatus of claim 6 wherein said face plates each have a header region in communication with said inlet and outlet port means and a plurality of elongated channels communicating with said header region and extending away therefrom, said channels opening into said interior chamber.

8. The gas transfer apparatus of claim 7 wherein said elongated channels diminish in cross-sectional size as they extend away from said header region.

9. The gas transfer apparatus of claim 6 wherein there are two pair of manifolds and wherein each of said face plates has two pair of opposed edges, said opposed edges of the face plates being secured to said manifolds to define said interior chamber, and wherein the ends of said fibers are open and potted in potting compounds which cooperate with the manifolds in fluidically separating the manifolds from each other and from the interior chamber such that said fluid being processed can be admitted to said apparatus through said inlet port means and removed from said apparatus through said outlet port means after having passed across the fibers of each set, and other fluids can be passed independently through each set of fibers.

10. The gas transfer apparatus of claim 4 wherein there are multiple layers of woven fibers with fibers of each set existing in each layer and with the fibers in each set extending substantially parallel to each other.

11. The gas transfer apparatus of claim 4 wherein the fibers of each set are substantially parallel, the mat is substantially quadrangular and wherein opposite ends of the fibers of each set are unwoven establishing notches in the four corners of the mat.

12. The gas transfer apparatus of claim 11 further including spacer means in each of said notches to render said mat truly quadrangular.

13. The gas transfer apparatus of claim 11 wherein the unwoven ends of said fibers are open and potted together with associated ends of corresponding fibers.

14. The gas transfer apparatus of claim 4 wherein said mat consists of a plurality of layers of fibers with fibers in each layer being of one set and extending in substantially parallel relationship, said layers of fibers being positioned and retained in face-to-face relationship.

15. The gas transfer apparatus of claim 14 wherein the fibers of each layer are bonded together with transverse beads of adhesive.

16. A gas transfer apparatus comprising in combination:
    a housing having spaced opposed face plates and four manifolds forming each of four sides of the housing while being sealed of the face plates along four side edges thereof, said face plates and manifolds cooperating to define an interior fluid processing chamber, an inlet pot and an outlet port establishing communication between said interior chamber and the environment surrounding said housing, connector means in each of said manifolds establishing communication between the manifolds and the environment surrounding said housing, and
    a mat of woven elongated hollow fibers disposed in said interior chamber and operatively associated with said housing to hermetically separate the manifolds from each other and from the interior chamber and to totally bridge the space between the two face plates, said mat being woven from two sets of substantially mutually perpendicular hollow fibers with the fibers of one set having walls with micropores formed therein to allow a gas to diffuse through the micropores into a fluid being processed and the fibers of the other set being liquid and gas impervious to selectively allow for the passage of a thermal transfer fluid, opposite ends of said fibers of each set being spoted in a potting compound and adapted to be seated in an associated manifold to define a hollow space within the manifold in communication with the connector means in the manifold, the ends of the fibers being open and in communication with the hollow space of the manifold with which the ends of the fibers are associated such that separate fluids can be passed through the fibers of each set between opposed manifolds while said fluid being processed is passed through the housing and across the mat via the inlet and outlet ports.

* * * * *

UNITED STATES PATENT AND TRADEMARK OFFICE
CERTIFICATE OF CORRECTION

PATENT NO. : 5,312,589
DATED : May 17, 1994
INVENTOR(S) : Gary D. Reeder, et. al.

It is certified that error appears in the above-indentified patent and that said Letters Patent is hereby corrected as shown below:

Column 6, line 45  "--Oxygen--" should read -- oxygen --

Column 7, line 50  "--housing 44--" should read -- housing 14 --

Column 10, line 39  "--fibers 60--" should read -- fibers 68 --

Column 11, line 13  "--ends--" should read -- ends, --

Column 12, line 30  "--of--" should read -- to --

Column 12, line 33  "--pot--" should read -- port --

Column 12, line 53  "--spoted--" should read -- potted --

Signed and Sealed this

Thirtieth Day of August, 1994

Attest:

Attesting Officer

BRUCE LEHMAN

Commissioner of Patents and Trademarks